United States Patent [19]
Goto et al.

[11] Patent Number: 5,116,743
[45] Date of Patent: May 26, 1992

[54] L-ALANINE PRODUCTION WITH TWO MICROORGANISMS HAVING FUMARASE INACTIVITY IN A SINGLE REACTION TANK

[75] Inventors: Makoto Goto; Terukazu Nara; Masato Terasawa; Hideaki Yukawa, all of Ami, Japan

[73] Assignee: Mitsubishi Petrochemical Co., Ltd., Tokyo, Japan

[21] Appl. No.: 790,063

[22] Filed: Nov. 12, 1991

Related U.S. Application Data

[63] Continuation of Ser. No. 474,508, Feb. 2, 1990, abandoned.

[30] Foreign Application Priority Data

Feb. 6, 1989 [JP] Japan ............................ 1-27044
Mar. 16, 1989 [JP] Japan ............................ 1-62089
Apr. 7, 1989 [JP] Japan ............................ 1-88267

[51] Int. Cl.⁵ .................. C12P 13/06; C12P 39/00; C12N 1/00; C12N 1/20
[52] U.S. Cl. .................................. 435/116; 435/874; 435/876; 435/877; 435/42; 435/109; 435/232; 435/193
[58] Field of Search ............... 435/116, 874, 876, 877, 435/42, 109, 232, 193

[56] References Cited

U.S. PATENT DOCUMENTS 3,898,128  8/1975  Chibata et al. .................. 435/116
3,933,586  1/1976  Duc .................................. 435/109

FOREIGN PATENT DOCUMENTS 53-27792   8/1978  Japan .
56-35991   4/1981  Japan .
57-132882  8/1982  Japan .
60-19997   5/1985  Japan .
60-126092  7/1985  Japan .
62-87088   4/1987  Japan .

OTHER PUBLICATIONS

Chang et al., "Some Stereochemical . . . ", vol. 257, No. 7, pp. 3564-3569, 1982.

Primary Examiner—David M. Naff
Assistant Examiner—Mike Meller
Attorney, Agent, or Firm—Oblon, Spivak, McClelland, Maier & Neustadt

[57] ABSTRACT

There is disclosed a process for producing L-alanine by reacting in a single reaction tank, in an aqueous reaction mixture having a pH of 6 to 10 and containing at least one α-keto acid, fumaric acid or a salt thereof with ammonia or ammonium ions in the presence of two microorganisms having fumarase inactivity.

13 Claims, No Drawings

L-ALANINE PRODUCTION WITH TWO MICROORGANISMS HAVING FUMARASE INACTIVITY IN A SINGLE REACTION TANK

This application is a continuation of application Ser. No. 07/474,508, filed on Feb. 2, 1990, now abandoned.

BACKGROUND OF THE INVENTION

This invention relates to a process for producing L-alanine enzymatically. According to the present invention, L-alanine can be produced in high yield with good efficiency.

L-alanine, as is well known in the art, is an important amino acid. It is used as a starting material for pharmaceuticals and foods and has other uses in the chemical industry. Its demand has abruptly increased in recent years.

For the industrial production of L-alanine, there has been proposed primarily a process for producing it by enzymatic decarboxylation of L-aspartic acid (Japanese Patent Publication No. 27792/1978) or a process for producing it from fumaric acid and ammonia by permitting aspartase (EC 4.3.1.1) and aspartate $\beta$-decarboxylase (EC.4.1.1.12) to act on these materials (Japanese Provisional Patent Publication No. 35991/1981). However, in the former process, L-aspartic acid which is the starting material is costly, resulting in higher production cost, while in the latter process, the optimum conditions such as pH and temperature in which both enzymes act are different, and therefore it is required that separate reaction tanks be used. Also, although both of enzymes can act in neutral pH, in that case, if microorganism cells or treated product thereof are used as the source of both enzymes, it is necessary to deactivate the enzyme presenting these materials which racemizes L-alanine co-present, and carry out the reaction at a relatively lower temperature (see Japanese Provisional Patent Publications No. 132882/1982, No. 87088/1987).

SUMMARY OF THE INVENTION

The present inventors have previously proposed a process for producing L-alanine from fumaric acid or a salt thereof and ammonia or ammonium ions in a single reaction tank under the co-presence of microorganism cells belonging to the genus Brevibacterium containing aspartase or the treated product thereof and microorganism cells belonging to the genus Pseudomonas containing L-aspartate $\beta$-decarboxylase or the treated product thereof (Japanese Patent Application No. 232570/1988).

The present inventors have further investigated reaction conditions, etc. which produce L-alanine with better efficiency, and found that part of the fumaric acid starting material is converted to L-malic acid through the action of fumarase (EC.4.1.-1.2) coexisting within the bacteria of the genus Pseudomonas, thereby reducing the yield of alanine. Hence, the present inventors have carried out intensive investigation to solve this problem, and consequently found that fumarase activity can be removed substantially completely without lowering aspartate $\beta$-decarboxylase activity which catalyzes the reaction from L-aspartic acid to L-alanine by subjecting the microorganism cells of the genus Pseudomonas or the treated product thereof, namely the crushed product of the cells to the heating treatment in a neutral aqueous solvent containing pyridoxal phosphate and/or an $\alpha$-keto acid or a salt thereof. Further, the present inventors have investigated intensively to improve the reaction rate of L-alanine formation, and consequently found that the reaction is made possible at a reaction temperature of 40° to 50° C. by adding at least an $\alpha$-keto acid into the reaction mixture in which aspartase and aspartate $\beta$-decarboxylase as mentioned above coexist, to accomplish the present invention.

Thus, according to the present invention, there is provided a process for producing L-alanine which comprises carrying out the reaction between fumaric acid or a salt thereof with ammonia or ammonium ions in an aqueous reaction mixture in a single reaction tank under the copresence of microorganism cells containing aspartase or the treated product thereof and microorganism cells containing aspartate $\beta$-decarboxylase to form L-alanine in said reaction mixture, characterized in that at least $\alpha$-keto acid is contained in said reaction mixture and the reaction is carried out at a reaction temperature of 40° to 50° C.

Also, there is provided a process for producing L-alanine as specified above, wherein the microorganism cells containing aspartate $\beta$-decarboxylase or the treated product thereof is subjected to a heating treatment in an aqueous solvent in the neutral region containing pyridoxal phosphate and/or an $\alpha$-keto acid or a salt thereof at temperature exceeding 40° C. and not higher than 60° C. before use for the reaction.

By use of the process of the present invention, the production of L-alanine in a single reaction tank is possible, and also L-alanine can be produced with good efficiency without converting some of the fumaric acid into L-malic acid through the reaction of fumarase coexisting within the microorganism cells, namely without bringing about loss of the starting material, and further at high reaction rate by maintaining the reaction temperature at 40° to 50° C. with a reaction mixture containing an $\alpha$-keto acid.

DESCRIPTION OF THE PREFERRED EMBODIMENTS

As the microorganism cells containing aspartase to be used in the present invention, any microorganism strain having said enzyme activity and belonging to the Coryne-form bacteria can be used. For example, there can be included *Brevibacterium flavum* MJ-233 (FERM BP-1497), *Brevibacterium flavum* MJ-233-AB-41 (FERM BP-1498), *Brevibacterium ammonigenes* ATCC 6872, *Corynebacterium glutamicum* ATCC 31830, etc., and these strains may be preferably used.

On the other hand, as the microorganism cells containing aspartate $\beta$-decarboxylase, any microorganism strain having this enzyme activity and belonging to the genus Pseudomonas can be used. For example, there can be included *Pseudomonas dacunhae* ATCC 21192, *Pseudomonas putida* ATCC 21812 and *Pseudomonas fluorescens* IFO 3081, and these strains may be preferably used.

Among these microorganisms, *Brevibacterium flavum* MJ-233 and *Brevibacterium flavum* MJ-233-AB-41 have been deposited under the terms of the Budapest Treaty under deposit numbers FERM BP-1497 and FERM BP-1498, respectively, at Fermentation Research Institute, Agency of Industrial Science and Technology, 1-3, Higashi 1-chome Tsukuba-shi, Ibaraki-ken 305, Japan. *Brevibacterium ammoniagenes* ATCC 6872, *Corynebacterium glutamicum* ATCC 31830, *Pseudomonas dacunhae* ATCC 21192 and *Pseudomonas putida* ATCC 21812 are microorganisms described in Type Culture Collection, Catalogue of Bacteria and Phages, seventeenth edition, 1989. *Pseudomonas fluorescens* IFO 3081 has been deposited at Institute for Fermentation Osaka, 17-85, Juso-honmachi 2-chome, Yodogawaku, Osaka 532, Japan. These microorganisms are freely available to the public.

The above-mentioned microorganism cells to be used in the present invention can be used as the cells as such, or also as the treated product thereof, namely as the crushed product of the cells.

As the method for crushing the cells, for example, known methods such as sonication treatment, squeezing, etc. can be utilized.

The carbon source for the medium to be used for preparation of microorganism cells containing aspartase is not particularly limited, but, for example, glucose, ethanol, organic acids such as acetic acid and fumaric acid can be used. As the nitrogen source for the medium, there can be used ammonia, ammonium sulfate, ammonium chloride, ammonium nitrate and urea, either alone or in a mixture. As the inorganic salt, there may be used potassium monohydrogen phosphate, potassium dihydrogen phosphate and magnesium sulfate. Otherwise, if necessary for growth of microorganisms, nutrients such as peptone, meat extract, yeast extract, corn steep liquor, casamino acids and various vitamins may be added in the medium.

Cultivation of the microorganism cells containing aspartase is carried out under aerobic conditions such as aeration stirring and shaking, and the cultivation temperature may be 20° to 40° C., preferably 25° to 35° C. The pH in the course of cultivation may be 5 to 10, preferably around 7 to 8, and the pH during cultivation may be adjusted with addition of an acid or an alkali. The cultivation time may be 2 to 9 days, with the optimum period being 4 to 7 days.

On the other hand, the carbon source for the medium to be used for preparation of the microorganism cells containing aspartate $\beta$-decarboxylase is not particularly limited, but fumaric acid, succinic acid and aspartic acid can be included, and among them, fumaric acid may be preferably used. As the nitrogen source for the medium, an inorganic salt such as ammonia, ammonium sulfate, ammonium chloride, ammonium nitrate and urea can be used, and also organic nutrient sources such as peptone, yeast extract, corn steep liquor and casamino acids can be also used. As the inorganic salt, there can be used potassium monohydrogen phosphate, potassium dihydrogen phosphate and magnesium sulfate.

Cultivation of the microorganism cells containing aspartate $\beta$-decarboxylase is carried out under aerobic conditions such as aeration stirring and shaking, and the cultivation temperature may be 20° to 40° C., preferably 28° C. to 32° C. The pH in the course of cultivation may be 5 to 10, preferably around 7 to 8, and the pH during cultivation may be adjusted with addition of an acid or an alkali. The fumaric acid concentration at initiation of cultivation may be preferably 0.1 to 5 % by weight, more preferably 0.5 to 2 % by weight. The cultivation period may be 10 hours to 4 days, with the optimum period being 1 to 3 days.

From the cultured products thus obtained, the respective microorganism cells are collected, washed with water or an appropriate buffer to practice the removal treatment of fumarase activity.

Since by-produced enzyme fumarase coexists also in the microorganism cells containing aspartase, when they are used in the production process of L-alanine of the present invention, it is desirable to previously removed fumarase activity.

As the method for removing fumarase activity coexisting into the microorganism cells containing aspartase, it can be practiced by heating the mixture to 40° to 60° C. under alkaline conditions, namely at a pH of 8 to 11, preferably a pH of 9 to 10, in the presence of L-aspartic acid and ammonium ions, and maintaining the mixture at about 5 minutes or longer, preferably about 10 minutes to about 16 hours, more preferably about 1 to about 10 hours.

The concentration of aspartic acid added can be 0.5 mole or more, preferably within the range from 0.7 to 5 moles, and the concentration of ammonium ions may be 1.0 to 4.0 gram ion/liter, preferably 1.4 to 3.0 gram ion/liter, more preferably 1.6 to 2.5 gram ion/liter (see Japanese Provisional Patent Publication No. 126092/1985).

On the other hand, the fumarase activity coexisting within the microorganism cells containing aspartate $\beta$-decarboxylase can be removed by suspending the microorganism cells prepared as described above or the treated product thereof in a neutral solvent such as water containing pyridoxal phosphate and/or an $\alpha$-keto acid or a phosphate buffer, and then heating the suspension.

In the aqueous solvent, at least pyridoxal phosphate and/or an $\alpha$-keto acid or a salt thereof is required to be contained. The concentration of pyridoxal phosphate which can be contained in the aqueous solvent may be 0.0001 to 0.5 % by weight, preferably 0.0005 to 0.1 % by weight, more preferably 0.001 to 0.05 % by weight.

The $\alpha$-keto acid or a salt thereof which can be contained in the aqueous solvent may include pyruvic acid or a salt thereof or $\alpha$-ketobutyric acid or a salt thereof. As the salt of pyruvic acid, sodium pyruvate, ammonium pyruvate, calcium pyruvate and potassium pyruvate may be included, and among them, sodium pyruvate is preferred. As the salt of $\alpha$-ketobutyric acid, sodium $\alpha$-ketobutyrate, ammonium $\alpha$-ketobutyrate, calcium $\alpha$-ketobutyrate and potassium $\alpha$-ketobutyrate may be included, and among them, sodium $\alpha$-ketobutyrate is preferred.

The concentration of the above-mentioned $\alpha$-keto acid or a salt thereof contained in said aqueous solvent may be 0.1 to 100 mM, preferably 0.5 to 50 mM, more preferably 1 to 20 mM.

The pH of the aqueous solvent preferably used may be the neutral region of 6.5 to 7.5. The heating treatment may be preferably practiced at a temperature exceeding 40° C. and within 60° C., particularly preferably at 45° to 50° C. The heating treatment time depends on the treatment temperature, but in the case of microorganism cells, generally 10 minutes to 24 hours, preferably 30 minutes to 10 hours, and in the case of the treated product of microorganism cells, suitably 5 minutes to 12 hours, preferably 20 minutes to 5 hours. The concentration of the microorganism cells or the treated product thereof in the aqueous solvent is not particularly limited, but generally 0.1 to 50 % by weight.

In the process of the present invention, the enzymatic reaction is carried out with an aqueous solution containing at least fumaric acid or a salt thereof and ammonia or ammonium ions and an $\alpha$-keto acid in a single reaction tank under the co-presence of the microorganism cells or the treated product thereof as prepared above. Here, the concentration of fumaric acid or a salt thereof to be added in said aqueous solution may be 0.5 to 30 % by weight, preferably 5 to 15 % by weight. As the concentration of ammonia or ammonium ions added, it may be 0.1 to 5M preferably 0.5 to 3.5M. As the salt of fumaric acid to be added in the aqueous solution, sodium fumarate, potassium fumarate and calcium fumarate may be included. Also as the ammonium ion source, ammonium chloride and ammonium sulfate may be included.

As the α-keto acid to be added in the reaction mixture, similar α-keto acids or salts thereof as mentioned above may be included, and among them, pyruvic acid or sodium salt thereof, or α-ketobutyric acid or sodium salt thereof may be preferably used. The concentration added may be 0.0001 to 0.5 % by weight, preferably 0.001 to 0.2 % by weight.

In said aqueous solution, pyridoxal phosphate can be further added in an amount of 0.0005 to 0.05 % by weight, preferably 0.001 to 0.01 % by weight. Further, if necessary, a nonionic surfactant such as polyoxyethylene (10) octyl phenyl ether (Triton X-100, trade name) and polyoxyethylene (20) sorbitane monolaurate (Tween 20, trade name) can be added in an amount of 0.01 to 0.5 % by weight, preferably 0.03 to 0.2 % by weight. In the present invention, the pH during the enzymatic reaction may be 6.0 to 10.0, preferably 7.0 to 8.5, the reaction temperature may be about 40° to about 50° C., preferably about 42° to about 47° C., and the reaction is carried out generally for about 5 to about 72 hours.

Separation and purification of L-alanine formed in the reaction mixture obtained according to the reaction method as described above can be practiced by known ion exchange resin treatment.

EXAMPLES

The following Referential examples and Examples illustrate the present invention more specifically. It should be understood that these examples are given as an aid to a specific recognition of the present invention, and do not limit the scope of the invention in any way.

In the following Referential examples and Examples, measurements of fumarase activity and aspartate β-decarboxylase, measurements of malic acid and L-alanine were performed as described below. The representation % means by weight.

(1) Fumarase Activity

Microorganism cells were suspended in 20 ml of a reaction mixture (containing fumaric acid: 830 mM, $CaCl_2.2H_2O$: 7.5 mM, polyoxyethylene (20) sorbitane monolaurate: 0.1 volume %, and ammonia: 2M, pH: 7.5), and shaken at 30° C. for 2 hours, and thereafter the amount of malic acid formed was measured to determine the activity.

(2) Aspartate β-Decarboxylase Activity

Microorganism cells were suspended in 20 ml of a reaction mixture (containing aspartic acid: 1500 mM, pyridoxal phosphate: 0.04 mM, polyoxyethylene (20) sorbitane monolaurate: 0.01 volume % and ammonia: 0.4M; pH: 4.7), shaken at 30° C. for one hour, and then the amount of alanine formed was measured to determine the activity.

(3) Malic Acid

Quantitated according to high performance liquid chromatography (Shimazu LC-5A, trade name, produced by Shimazu Seisakusho K.K.).

(4) L-alanine

Qualitatively confirmed from the Rf value of the paper chromatography, the retention time of high performance liquid chromatography and the specific rotation of the purified product. Quantitative analysis was performed with high performance liquid chromatography (Shimazu LC-5A, produced by Shimazu Seisakusho K.K.).

REFERENTIAL EXAMPLE 1

A) Culturing of *Brevibacterium flavum* MJ-233 Cells

An amount 100 ml of a culture medium (urea: 0.4%, ammonium sulfate: 1.4%, $KH_2PO_4$: 0.05%, $K_2HPO_4$: 0.05%, $MgSO_4.7H_2O$: 0.05%, $CaCl_2.2H_2O$: 2 ppm, $FeSO_4.7H_2O$: 2 ppm, $MnSO_4.4-6H_2O$: 2 ppm, $ZnSO_4.7H_2O$: 2 ppm, NaCl: 2 ppm, biotin: 200 μg/liter, thiamine.HCl: 100 μg/liter, casamino acids: 0.1%, yeast extract: 0.1%) was apportioned into an Erlenmeyer's flask of 500 ml volume, and after sterilization, *Brevibacterium flavum* MJ-233 (FERM BP-1497) was inoculated and 2 ml of ethanol was added aseptically, followed by shaking cultivation at 30° C. for 2 days.

Next, 1000 ml of main culture medium (ammonium sulfate: 2.3%, $KH_2PO_4$: 0.05%, $K_2HPO_4$: 0.05%, $MgSO_4.7H_2O$: 0.05%, $FeSO_4.7H_2O$: 20 ppm, $MnSO_4.4-6H_2O$: 20 ppm, biotin: 200 μg/liter, thiamine.HCl: 100 μg/liter, casamino acids: 0.3%, yeast extract: 0.3%) was charged into a 2-liter volume tank under aerated stirring, and after sterilization (120° C., 20 minutes), 20 ml of ethanol and 20 ml of the above cultured product were added, followed by cultivation at a rotational number of 1000 rpm, an aeration amount of 1 vvm, a temperature of 33° C. and a pH of 7.6 for 48 hours.

Ethanol was added intermittently every about 1 to 2 hours so that the concentration in the medium during cultivation did not exceed 2 volume %, until it was added finally to 100 ml.

After completion of the cultivation, the cells were collected by centrifugation from 1000 ml of the cultured product.

B) Removal Treatment of Fumarase Activity

Since by-produced enzyme fumarase coexists within the microorganism cells prepared in the above item A) in addition to aspartase, there ensues the problem of conversion of fumaric acid which is the starting material partially into malic acid, and therefore removal treatment of fumarase activity was previously practiced.

The microorganism cells prepared in the above item A) were suspended in one liter of a reaction mixture (L-aspartic acid: 100 g, ammonia (aqueous solution containing 28% ammonia): 140 ml, $CaCl_2.2H_2O$: 1 g, polyoxyethylene (20) sorbitane monolaurate: 0.8 g; contained in one liter of distilled water), and the heating treatment was conducted at 45° C. for 5 hours. Said treated product was subjected to collection of cells by centrifugation, and said cells were used as the aspartase containing cells.

REFERENTIAL EXAMPLE 2

A) Culturing of *Brevibacterium ammoniagenes* ATCC 6872 Cells

After 100 ml of the preparation medium of the aspartase containing microorganism cells used in Referential example 1 was apportioned into an Erlenmeyer's flask of 500 ml volume and sterilized (pH 7 after sterilization), *Brevibacterium ammoniagenes* ATCC 6872 was inoculated, and 2 ml of 50 % of glucose was aseptically added, followed by shaking cultivation at 30° C. for 24 hours.

Next, similarly 1000 ml of the main culture medium in Referential example 1 was charged into a 2-liter volume tank under aerated stirring, and after sterilization (120° C., 20 minutes), 40 ml of 50 % of glucose and 20 ml of the above cultured product were added, followed by cultivation at a rotational number of 1000 rpm, an aeration amount of 1 vvm, a temperature of 33° C. and a pH of 7.6 for 24 hours.

The glucose was added in an amount of 5 g every about 1 to 2 hours, until added finally up to 70 g.

After completion of the cultivation, the cells were collected by centrifugation from 1000 ml of the cultured product.

B) Removal Treatment of Fumarase Activity

The microorganism cells prepared in the above item A) were suspended in one liter of the reaction mixture used in the item B) of Referential example 1, and then the heating treatment was conducted at 45° C. for 2 hours. Said treated product was subjected to collection of cells, and said cells were used as the aspartase containing cells.

REFERENTIAL EXAMPLE 3

A) Culturing of *Corynebacterium glutamicum* ATCC 31830 Cells

After 100 ml of the preparation medium of the aspartase containing microorganism cells used in Referential example 1 was apportioned into an Erlenmeyer's flask of 500 ml volume and sterilized (pH 7 after sterilization), *Corynebacterium glutamicum* ATCC 31830 was inoculated, and 2 ml of 50 % of glucose was aseptically added, followed by shaking cultivation at 30° C. for 24 hours.

Next, similarly 1000 ml of the main culture medium in Referential example 1 was charged into a 2-liter volume tank under aerated stirring, and after sterilization (120° C., 20 minutes), 40 ml of 50 % of glucose and 20 ml of the above cultured product were added, followed by cultivation at a rotational number of 1000 rpm, an aeration amount of 1 vvm, a temperature of 33° C. and a pH of 7.6 for 24 hours.

The glucose was added in an amount of 5 g every about 1 to 2 hours, until added finally up to 70 g.

After completion of the cultivation, the cells were collected by centrifugation from 1000 ml of the cultured product.

B) Removal Treatment of Fumarase Activity

The microorganism cells prepared in the above item A) were suspended in one liter of the reaction mixture used in the item B) of Referential example 1, and then the heating treatment was conducted at 45° C. for 2 hours. Said treated product was subjected to collection of cells, and said cells were used as the aspartase containing cells.

EXAMPLE 1

A) Culturing of *Pseudomonas dacunhae* ATCC 21192 Cells

An amount 100 ml of a medium (containing sodium fumarate: 0.5%, ammonium fumarate: 1.0%, yeast extract: 0.5%, potassium monophosphate: 0.05%, $MgSO_4.7H_2O$: 0.05%, pH: 7.0) was apportioned into an Erlenmeyer's flask of 500 ml volume, and after sterilization, *Pseudomonas dacunhae* ATCC 21192 was inoculated and subjected to shaking cultivation (pre-culturing) at 30° C. for one day. Next, one liter of the same medium as the above medium was charged into a 2-liter volume tank under aerated stirring and, after sterilization (120° C., 20 minutes), 20 ml of the pre-cultured product was added and cultivated at a rotational number of 1000 rpm, an aeration amount of 1 vvm, a temperature of 30° C. and a pH of 7.3 for one day.

After completion of the cultivation, the cells were collected by centrifugation from 100 ml of the cultured product, and said cells were used for removal treatment of fumarase activity.

B) Removal of Fumarase Activity

The cells prepared in the above item A) were added into 100 ml of a 10 mM phosphate buffer of pH 7.5 containing 10 mg/liter of pyridoxal phosphate, and heating treatment was conducted under various conditions. The heat treated cells were collected by centrifugation, and fumarase activity and aspartate $\beta$-decarbocarboxylase activity of said cells were measured. The respective enzyme activity values are represented in terms of relative activity to the activity of the cells which are not subjected to heating treatment as 100.

The results are shown in Table 1.

TABLE 1

| Treatment temperature (°C.) | Treatment time (hr) | Fumarase activity (%) | Aspartate $\beta$-decarboxylase activity (%) |
|---|---|---|---|
| 45 | 5 | 15 | 99 |
|  | 9 | 5 | 99 |
| 50 | 1 | 18 | 99 |
|  | 2 | <0.5 | 98 |

In Examples 5 to 10, *Pseudomonas daunhae* ATCC 21192 was cultured similarly as described above, and subjected to the heat treatment at 50° C. for 2 hours, the microorganism cells were collected by centrifugation and said cells were used as aspartate $\beta$-decarboxylase containing cells.

By this heating treatment in an aqueous solvent in the neutral region (pH 7.5) containing pyridoxal phosphate, fumarase activity could be removed substantially completely without lowering the aspartate $\beta$-decarboxylase activity.

EXAMPLE 2

The same experiment as in Example 1 was conducted except for using 5 mM of sodium pyruvate in place of 10 mg/liter, pyridoxal phosphate used in the item B) in Example 1.

The results are shown in Table 2.

TABLE 2

| Treatment temperature (°C.) | Treatment time (hr) | Fumarase activity (%) | Aspartate $\beta$-decarboxylase activity (%) |
|---|---|---|---|
| 45 | 5 | 14 | 99 |
|  | 9 | 4 | 99 |
| 50 | 1 | 16 | 99 |
|  | 2 | <0.5 | 98 |

By this heating treatment in an aqueous solvent in the neutral region (pH 7.5) containing sodium pyruvate, fumarase activity could be removed substantially completely without lowering the aspartate β-decarboxylase activity.

EXAMPLE 3

The same experiment as in Example 1 was conducted except for using 5 mM of sodium α-ketobutyrate in place of 10 mg/liter of pyriodoxal phosphate used in the item B) in Example 1.

The results are shown in Table 3.

TABLE 3

| Treatment temperature (°C.) | Treatment time (hr) | Fumarase activity (%) | Aspartate β-decarboxylase activity (%) |
|---|---|---|---|
| 45 | 5 | 15 | 99 |
|  | 9 | 5 | 98 |
| 50 | 1 | 16 | 99 |
|  | 2 | <0.5 | 98 |

By this heating treatment in an aqueous solvent in the neutral region (pH 7.5) containing sodium α-ketobutyrate, fumarase activity could be removed substantially completely without lowering the aspartate β-decarboxylase activity.

EXAMPLE 4

The same experiment as in Example 1 was conducted except for using 10 mg/liter of pyridoxal phosphate and 5 mM of sodium pyruvate in place of 10 mg/liter of pyridoxal phosphate used in the item B) in Example 1.

The results are shown in Table 4.

TABLE 4

| Treatment temperature (°C.) | Treatment time (hr) | Fumarase activity (%) | Aspartate β-decarboxylase activity (%) |
|---|---|---|---|
| 45 | 6 | 11 | 99 |
|  | 10 | 3 | 99 |
| 50 | 1 | 9 | 99 |
|  | 2 | <0.5 | 99 |

By this heating treatment in an aqueous solvent in the neutral region (pH 7.5) containing pyridoxal phosphate and sodium pyruvate, fumarase activity could be removed substantially completely without lowering the aspartate β-decarboxylase activity.

EXAMPLE 5

The respective microorganism cells collected by centrifugation from 200 ml of the suspensions of microorganism cells prepared in the item B) of Referential Example 1 and the item B) of Example 1 were combined, suspended in 200 ml of a reaction mixture (fumaric acid: 1M, aqueous ammonia: 2.8M, sodium pyruvate: 5 mM, pyridoxal phosphate: 0.04 mM, polyoxyethylene (20) sorbitane monolaurate: 0.05%, pH: 7.5) and then charged into a one liter tank under aerated stirring, followed by the reaction under the conditions shown in Table 5 at a stirring rotational number of 300 rpm for 20 hours.

After completion of the reaction, the alanine formed in the reaction mixture was quantitated. The results are shown in Table 5. After 100 ml of said reaction mixture after completion was adjusted to pH 4.0, it was subjected to boiling filtration and the filtrate was passed through Amberlite IRC-50 (trade name, H+form), washed with water and subsequently eluted with 4.5 % aqueous ammonia. The eluted solution was concentrated under reduced pressure and then the crystals were precipitated with cold ethanol. The amount of L-alanine recovered is shown in Table 5. Further, when the specific optical rotations of the recovered alanines were measured, all were found to be $[\alpha]_D^{23} = +14.3°$ (C=10, 6N-HCl).

Also, as Comparative example, the amount of L-alanine formed when no sodium pyruvate was added in the reaction mixture is shown together in Table 5.

TABLE 5

| Reaction temperature (°C.) | Addition of sodium pyruvate | Amount of L-alanine formed (mg/ml) | Amount of L-alanine recovered (mg) |
|---|---|---|---|
| 37 | + | 58 | 3070 |
|  | − | 57 | 3030 |
| 40 | + | 71 | 3800 |
|  | − | 56 | 3000 |
| 42 | + | 83 | 4480 |
|  | − | 45 | 2470 |
| 47 | + | 85 | 4490 |
|  | − | 40 | 2120 |
| 50 | + | 65 | 3570 |
|  | − | 20 | 1060 |

By use of the process of this example, L-alanine was produced effectively from fumaric acid and ammonia in a single reaction tank in the presence of *Brevibacterium flavum* MJ-233 cells and *Pseudomonas dacunhae* ATCC 21192 cells.

EXAMPLE 6

The same experiment as in Example 5 was conducted except for changing sodium pyruvate in the reaction mixture in Example 5 to 5 mM of sodium α-ketobutyrate. The results are shown in Table 6.

The specific optical rotation of the L-alanine recovered was found to be $[\alpha]_D^{23} = +14.3°$ (C=10, 6N-HCl).

TABLE 6

| Reaction temperature (°C.) | Addition of sodium α-ketobutyrate | Amount of L-alanine formed (mg/ml) | Amount of L-alanine recovered (mg) |
|---|---|---|---|
| 37 | + | 55 | 2860 |
|  | − | 55 | 2850 |
| 40 | + | 68 | 3580 |
|  | − | 53 | 2800 |
| 42 | + | 85 | 4500 |
|  | − | 43 | 2240 |
| 47 | + | 84 | 4450 |
|  | − | 33 | 1750 |
| 50 | + | 65 | 3550 |
|  | − | 15 | 800 |

By use of the process of this example, L-alanine was produced effectively from fumaric acid and ammonia in a single reaction tank in the presence of *Brevibacterium flavum* MJ-233 cells and Pseudomonas dacunhae ATCC 21192 cells.

EXAMPLE 7

The reaction and the purification were conducted in the same manner as in Example 5 by use of the respective microorganism cells collected from 200 ml of the suspensions of the cells prepared in the item B) of Referential Example 2 and the item B) of Example 1. The amount of L-alanine recovered are shown in Table 7. Further, when the specific optical rotation of the alanine recovered was measured, it was found to be $[\alpha]_D^{25} = +14.4°$ (C=10, 6N-HCl).

TABLE 7

| Reaction temperature (°C.) | Addition of sodium pyruvate | Amount of L-alanine formed (mg/ml) | Amount of L-alanine recovered (mg) |
| --- | --- | --- | --- |
| 37 | + | 35 | 1900 |
|    | − | 31 | 1620 |
| 40 | + | 45 | 2380 |
|    | − | 33 | 1760 |
| 42 | + | 48 | 2540 |
|    | − | 35 | 1830 |
| 47 | + | 52 | 2750 |
|    | − | 30 | 1600 |
| 50 | + | 40 | 2100 |
|    | − | 19 | 1000 |

By use of the process of this example, L-alanine was produced effectively from fumaric acid and ammonia in a single reaction tank in the presence of *Brevibacterium ammoniagenes* ATCC 6872 cells and *Pseudomonas dacunhae* ATCC 21192 cells.

EXAMPLE 8

The same experiment as in Example 7 was conducted except for changing sodium pyruvate in Example 7 to 5 mM of sodium α-ketobutyrate.

The specific optical rotation of the L-alanine recovered was found to be $[\alpha]_D^{25} = +14.4°$ (C=10, 6N-HCl).

The results are shown in Table 8.

TABLE 8

| Reaction temperature (°C.) | Addition of sodium α-ketobutyrate | Amount of L-alanine formed (mg/ml) | Amount of L-alanine recovered (mg) |
| --- | --- | --- | --- |
| 37 | + | 33 | 1750 |
|    | − | 30 | 1580 |
| 40 | + | 44 | 2330 |
|    | − | 32 | 1690 |
| 42 | + | 47 | 2490 |
|    | − | 37 | 1960 |
| 47 | + | 53 | 2805 |
|    | − | 29 | 1530 |
| 50 | + | 41 | 2170 |
|    | − | 18 | 950 |

By use of the process of this example, L-alanine was produced effectively from fumaric acid and ammonia in a single reaction tank in the presence of *Brevibacterium ammoniagenes* ATCC 6872 cells and *Pseudomonas dacunhae* ATCC 21192 cells.

EXAMPLE 9

The reaction and the purification were conducted in the same manner as in Example 5 by use of the respective microorganism cells collected from 200 ml of the suspensions of the cells prepared in the item B) of Referential Example 3 and the item B) of Example 1. The amount of L-alanine recovered are shown in Table 9. Further, when the specific optical rotation of the alanine recovered was measured, it was found to be $[\alpha]_D^{25} = +14.3°$ (C=10, 6N-HCl).

TABLE 9

| Reaction temperature (°C.) | Addition of sodium pyruvate | Amount of L-alanine formed (mg/ml) | Amount of L-alanine recovered (mg) |
| --- | --- | --- | --- |
| 37 | + | 34 | 1800 |
|    | − | 31 | 1640 |
| 40 | + | 48 | 2540 |
|    | − | 34 | 1790 |
| 42 | + | 52 | 2750 |
|    | − | 36 | 1900 |
| 47 | + | 58 | 3070 |

TABLE 9-continued

| Reaction temperature (°C.) | Addition of sodium pyruvate | Amount of L-alanine formed (mg/ml) | Amount of L-alanine recovered (mg) |
| --- | --- | --- | --- |
|    | − | 31 | 1640 |
| 50 | + | 41 | 2170 |
|    | − | 21 | 1100 |

By use of the process of this example, L-alanine was produced effectively from fumaric acid and ammonia in a single reaction tank in the presence of *Corynebacterium glutamicum* ATCC 31830 cells and *Pseudomonas dacunhae* ATCC 21192 cells.

EXAMPLE 10

The same experiment as in Example 9 was conducted except for changing sodium pyruvate in Example 9 to 5 mmole of sodium α-ketobutyrate.

The specific optical rotation of the L-alanine recovered was found to be $[\alpha]_D^{25} = +14.3°$ (C=10, 6N-HCl).

The results are shown in Table 10.

TABLE 10

| Reaction temperature (°C.) | Addition of sodium α-ketobutyrate | Amount of L-alanine formed (mg/ml) | Amount of L-alanine recovered (mg) |
| --- | --- | --- | --- |
| 37 | + | 34 | 1800 |
|    | − | 31 | 1630 |
| 40 | + | 46 | 2430 |
|    | − | 33 | 1740 |
| 42 | + | 50 | 2630 |
|    | − | 39 | 2050 |
| 47 | + | 56 | 2930 |
|    | − | 30 | 1580 |
| 50 | + | 39 | 2060 |
|    | − | 20 | 1050 |

By use of the process of this example, L-alanine was produced effectively from fumaric acid and ammonia in a single reaction tank in the presence of *Corynebacterium glutamicum* ATCC 31830 cells and *Pseudomonas dacunhae* ATCC 21192 cells.

We claim:

1. A process for producing L-alanine by reacting, in a single reaction tank, in an aqueous reaction mixture having a pH of 6 to 10 and containing at least one alpha-keto acid, and at a temperature of 40° C. to 50° C. fumaric acid or a salt thereof with ammonia or ammonium ions in the presence of cells of a first microorganism and cells of a second microorganism, and thereby obtaining L-alanine, wherein:
(i) said cells of said first microorganism contain aspartase but no fumarase activity due to having been subjected to a heating treatment under alkaline conditions at a temperature of from 40° C. to 60° C. in the presence of L-aspartic acid and ammonium ions;

wherein said first microorganism cells are *Brevibacterium flavum* MJ-233 (FERM BP-1497), *Brevibacterium flavum* MJ-233-AB-41 (FERM BP-1498), *Brevibacterium ammoniagenes* ATCC 6872 or *Corynebacterium glutamicum* ATCC 31830; and (ii) said cells of said second microorganism contain aspartate beta-decarboxylase but no fumarase activity due to having been subjected to a heating treatment, at a pH of 6.5 to 7.5, in an aqueous solvent containing pyridoxal phosphate or an alpha-keto acid, or both, or a salt thereof, and at a temperature of over 40° C. and up to 60° C.; wherein said second microorganism cells are *Pseudomonas dacunhae* ATCC 21192, *Pseudomonas putida* ATCC 21812 or *Pseudomonas fluorescens* IFO 3081.

2. A process according to claim 1, wherein the concentration of pyriodoxal phosphate in the aqueous solvent is within the range from 0.001 to 0.5% by weight.

3. A process according to claim 1, wherein the concentration of the α-keto acid or the salt thereof is within the range from 0.1 to 100 mM.

4. A process according to claim 1, wherein the heating treatment temperature of the microorganism cells containing aspartate α-decarboxylase or the treated product thereof is within the range from 45° to 50° C.

5. A process according to claim 1, wherein the α-keto acid or the salt thereof in the aqueous reaction mixture is pyruvic acid or a salt thereof, or an α-ketobutyric acid or a salt thereof.

6. A process according to claim 1, wherein the concentration of the α-keto acid or the salt thereof in the aqueous reaction mixture is within the range from 0.0001 to 0.5 % by weight.

7. A process according to claim 1, wherein the reaction temperature is within the range from about 42° to about 47° C.

8. A process according to claim 1, wherein the concentration of fumaric acid or the salt thereof in the aqueous reaction mixture is within the range from 0.5 to 30% by weight.

9. A process according to claim 1, wherein the reaction is carried out in the co-presence of pyridoxal phosphate in the aqueous reaction mixture.

10. A process according to claim 9, wherein the concentration of pyridoxal phosphate is within the range from 0.0005 to 0.05 % by weight.

11. A process according to claim 1, wherein the reaction is carried out in the co-presence of a nonionic surfactant in the aqueous reaction mixture.

12. A process according to claim 11, wherein said nonionic surfactant is polyoxyethylene (20) sorbitane monolaurate or polyoxyethylene (10) octyl phenyl ether.

13. A process according to claim 11, wherein the concentration of said nonionic surfactant is within the range from 0.01 to 0.5% by weight.

* * * * *